United States Patent [19]

Chern

[11] Patent Number: 5,124,640
[45] Date of Patent: Jun. 23, 1992

[54] METHOD FOR ADVANCED MATERIAL CHARACTERIZATION BY LASER INDUCED EDDY CURRENT IMAGING

[75] Inventor: Engmin J. Chern, Columbia, Md.

[73] Assignee: The United States of Americas as represented by the Administrator of the National Aeronautics & Space Administration, Washington, D.C.

[21] Appl. No.: 758,977

[22] Filed: Sep. 5, 1991

[51] Int. Cl.$^5$ ............... G01R 35/00; G01R 31/00; G01N 27/14; G01N 27/20

[52] U.S. Cl. ............... 324/224; 324/226; 324/262; 356/432; 374/4; 374/45

[58] Field of Search ............ 324/224, 226, 262, 501, 324/693, 702, 703, 158 R, 158 D; 356/432 T; 374/4, 6, 7, 45, 57

[56] References Cited

U.S. PATENT DOCUMENTS 4,950,990  8/1990  Moulder et al. ............... 324/224

OTHER PUBLICATIONS

International Advances in Nondestructive Testing, 1989, pp. 175–218.
McGraw-Hill Encyclopedia of Science & Technology, vol. 11, 1987, pp. 28–33.
Review of Progress in Quantititative Nondestructive Evaluation, vol. 9, 1990, pp. 533–538.

*Primary Examiner*—Walter E. Snow
*Attorney, Agent, or Firm*—R. Dennis Marchant; Guy M. Miller; Paul S. Clohan

[57] ABSTRACT

An improved NDE method utilizes a laser source with modulator and scanning mirror, a pancake shape eddy current detecting coil, a lock-in amplifier, a system controller, and an impedance gain/phase analyzer. The laser is directed by the scanning mirror to a specimen to be analyzed. A very localized or small area of the specimen is impacted directly by the laser beam creating a thermal and stress wave in the specimen. An impedance gain/phase analyzer is connected to the eddy current detecting coil and to a lock-in amplifier through the system controller. The lock-in amplifier is also synchronized to the laser modulator. The system controller is used to control the lock-in amplifier, scanning mirror, and to process data from the analyzer. Raster scanning of the laser beam across the speciment allows the detection by the coil of the laser generated thermal and elastic strains induced in the specimen by the laser. The rastering of the laser beam is controlled by the controller by positioning the mirror.

4 Claims, 3 Drawing Sheets

METHOD FOR ADVANCED MATERIAL CHARACTERIZATION BY LASER INDUCED EDDY CURRENT IMAGING

ORIGIN OF THE INVENTION

The invention described herein was made by an employee of the United States Government, and may be manufactured and used by or for the Government for governmental purposes without the payment of any royalties thereon or therefor.

TECHNICAL FIELD

This invention relates to Nondestructive Evaluation and in particular to a system utilizing an eddy current imaging system for the detection of laser generated thermal and elastic strains in materials for advanced material characterization.

BACKGROUND ART

Nondestructive Evaluation (NDE) uses tests to examine an object or material to detect imperfections, determine properties, or asses quality without changing its usefulness. NDE methods have been developed over the years using high powered optical techniques, ultrasonic surface wave measurement, stress fluorescent, penetrant techniques, and eddy current inspection analysis. This invention is primarily concerned with utilizing an eddy current imaging system for the detection of laser generated thermal and elastic strains in materials for advanced material characterization. This advanced technology can be used for surface displacement evaluation, defect detection and damage assessment.

Eddy-current probes have been used in the past as a form of NDE and recently in conjunction with photoinductive imaging. Photoinductive imaging is a unique dual-mode NDE technique that combines eddy current and thermal wave methods. The photoinductive effect, upon which this method is based, is the thermally induced change in the impedance of an eddy current probe in proximity to a conducting surface that is illuminated with a modulated light source. The change in probe impedance is caused by the temperature-induced changes in the conductivity and permeability of the specimen. Typical changes in probe impedance are small, on the order of a few ppm, but because they are synchronous with the light-beam modulation, lock-in techniques can be used to detect the signals, which can then be used to image surface or near-surface defects, voids, inclusions, or other thermal or structural inhomogeneities. The problems with the prior art photoinductive NDE has been that they offer only one side excitation and detection on the specimen and can only be used to examine very thin surface features within submicrons.

STATEMENT OF THE INVENTION

It is therefore an object of the present invention to provide an improved method and apparatus for the detection of thermal strains in sample materials.

Another object of the invention is to provide an improved Nondestructive Evaluation technique.

A still further object of the invention is to provide an improved method for advanced materials characterization.

The foregoing objects and others are achieved by providing an improved NDE method utilizing five major hardware components: a laser source with modulator and scanning mirror, a pancake shape eddy current detecting coil, a lock-in amplifier, a system controller, and an impedance gain/phase analyzer. The laser is directed by the scanning mirror to a specimen to be analyzed. A very localized or small area of the specimen is impacted directly by the laser beam creating a thermal and stress wave in the specimen. Depth penetration by the thermal wave is dependent on the modulation frequency of the laser modulator.

An impedance gain/phase analyzer is connected to the eddy current detecting coil and to a lock-in amplifier through the system controller. The lock-in amplifier is also synchronized to the laser modulator. The system controller is used to control the lock-in amplifier, scanning mirror, and to process data from the analyzer. Raster scanning of the laser beam across the specimen allows the detection by the coil of the laser generated thermal and elastic strains induced in the specimen by the laser. The rastering of the laser beam is controlled by the controller by positioning the mirror.

The method of detection of flaws in the present invention differs from that in the prior art. The present inventive technique uses the absolute resistance and inductance of the detector coil vs. the arbitrary proportional signals of the prior art.

DETAILED DESCRIPTION OF THE INVENTION

Figure 1:
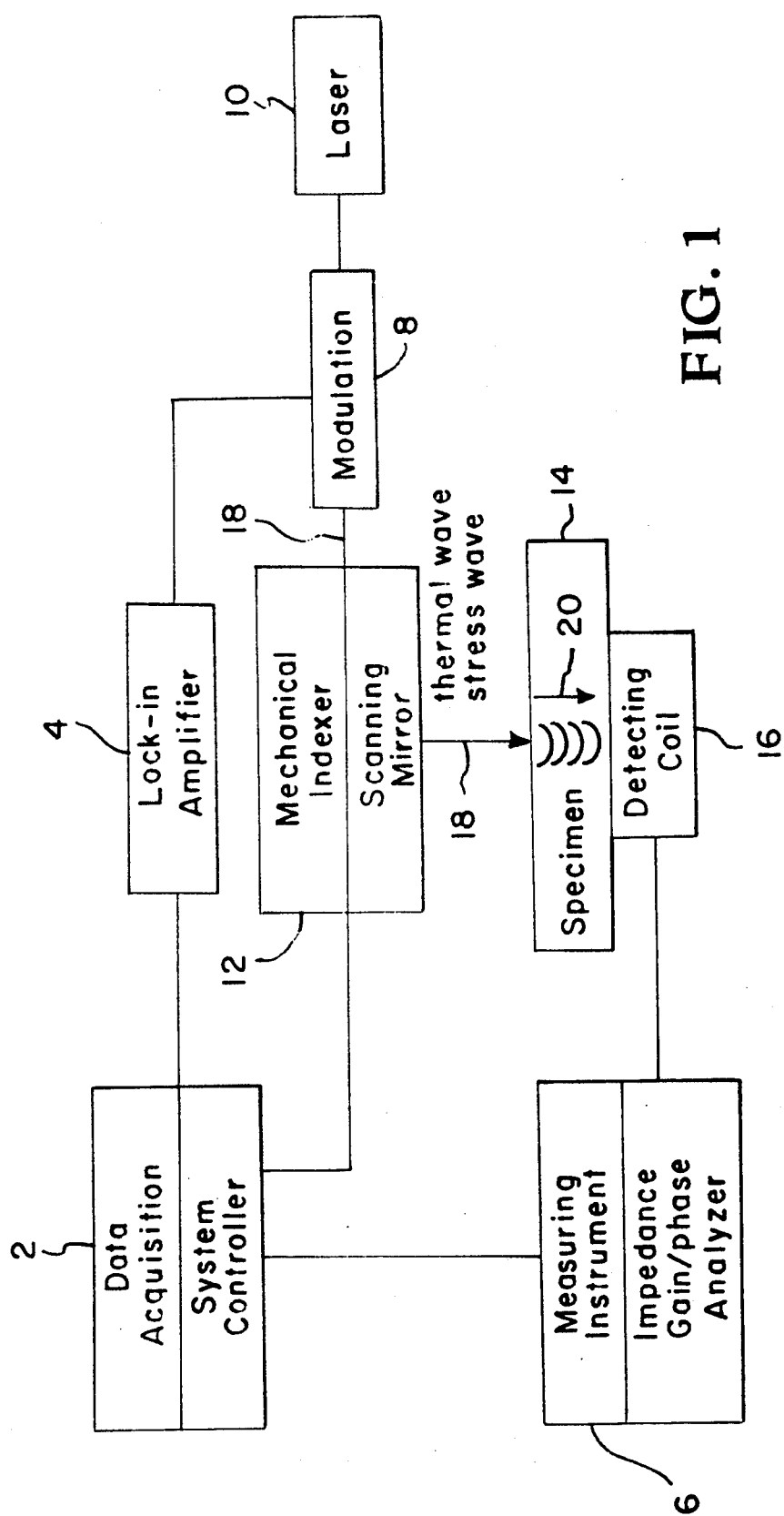
FIG. 1 is a block diagram of the components of the present invention.
Figure 2:
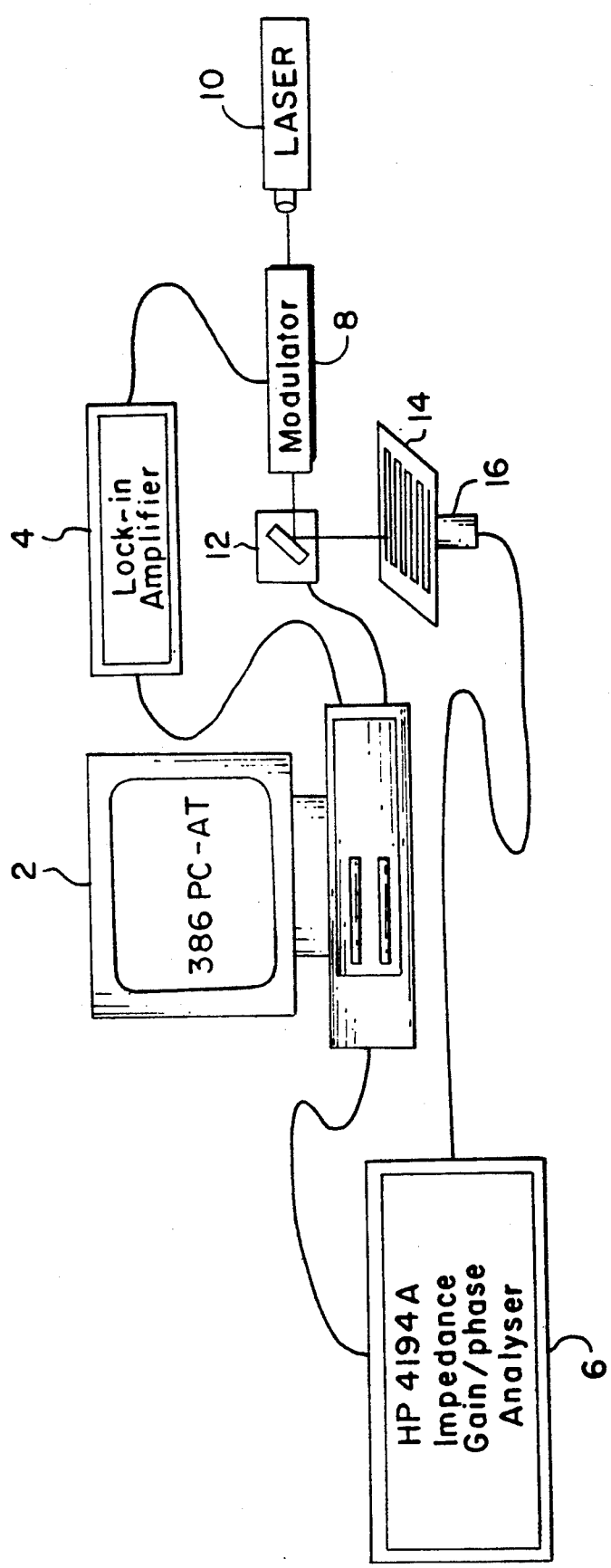
FIG. 2 is a pictorial representation of the operation of the present invention.

The invention consists of an improved method utilizing five major hardware components as shown in FIG. 1, which is a block diagram of the present inventive system for laser induced eddy current imaging. The five major components are: a laser source 10, a pancake shape eddy current detecting coil 16, a lock-in amplifier 4, a system controller 2, and an impedance gain/phase analyzer 6. Other sub-components are modulator 8, scanning mirror 12 and specimen 14.

Figure 4:
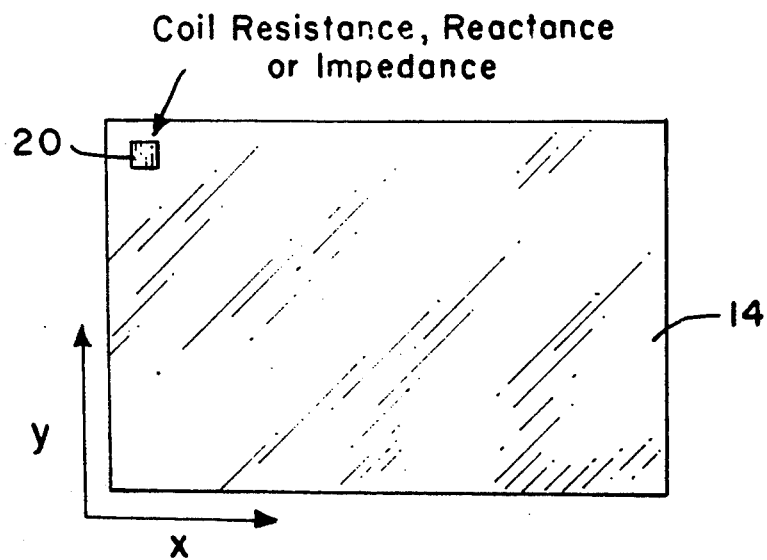
FIG. 4 is a plan view of a specimen to be scanned by the present inventive technique.

Laser 10 is the excitation source and can be an argon-ion laser or another suitable laser. Laser 10 is modulated by modulator 8, which is essentially a cyclic function generator, producing a beam 18 which is directed by scanning mirror 12 to specimen 14. As shown in FIG. 4, a very localized or small area 20 of specimen 14 is impacted directly by beam 18, creating a thermal and stress wave 20 in specimen 14 and inducing thermal and elastic strains in specimen 14. Depth penetration by wave 20 is dependent upon the modulation frequency of modulator 8.

An impedance gain/phase analyzer 6, such as is well known in the art, is connected to eddy current detecting coil 16. Analyzer 6 is in turn connected to lock-in amplifier 4 through system controller 2. The lock-in amplifier 4 is also synchronized to modulator 8. System controller 2 is used to control lock-in amplifier 4, scanning mirror 12, and to process data from analyzer 6. System controller can be an IBM series 386 PC or the equivalent. An example of a suitable impedance gain/phase analyzer 6 is an HP 4194A analyzer connected by an IEEE488 bus to controller 2. A typical eddy current detecting coil 16 is a Nortec surface probe SP-100. Lock-in amplifiers are well known in this art.

Figure 3:
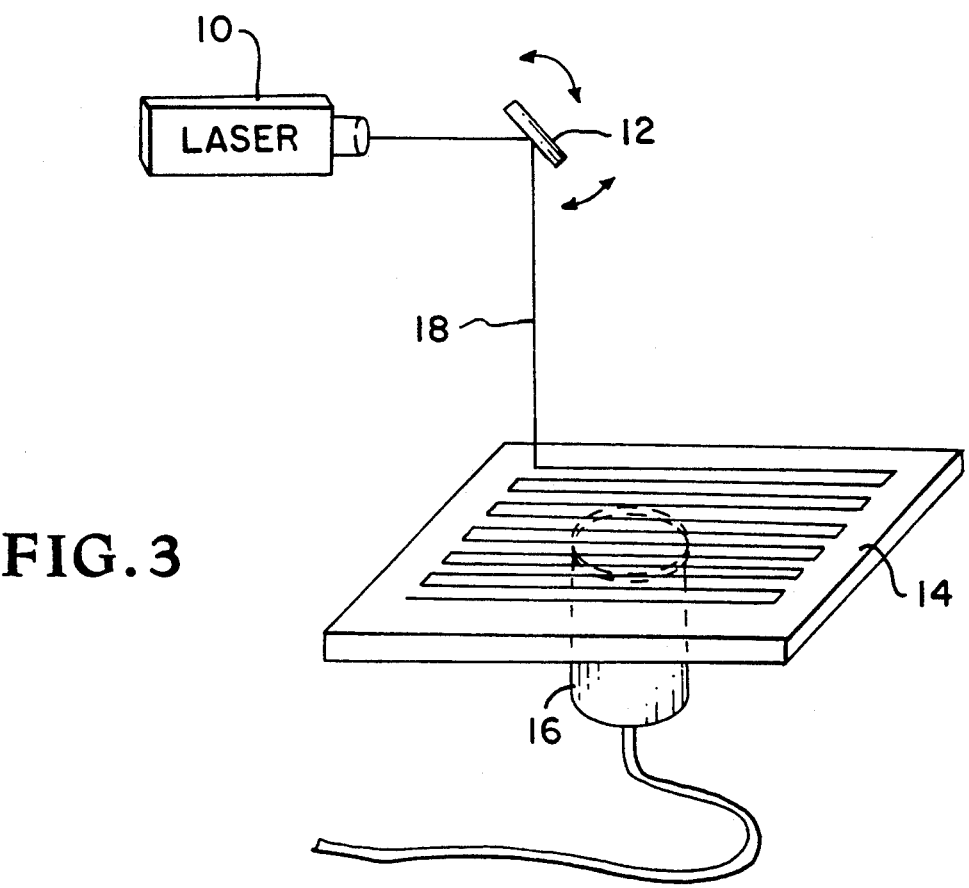
FIG. 3 is a perspective view of a portion of the present invention.

FIG. 3 shows the raster scanning of beam 18 across specimen 14 which allows the detection by coil 16 of the laser generated thermal and elastic strains induced in specimen 14 by laser 10 The rastering of beam 18 is controlled by controller 2 by positioning mirror 12. This technique is well known in the art.

The method of detection of flaws in the present invention differs from that in the prior art as follows. In the prior art, signals from the lock-in amplifier resulted in a magnitude component and a phase component. Each of these components was sent to separate volt meters from the lock-in amp. The analog output signals of the volt meters was then summed with a signals from vertical and horizontal position sensors and fed into the vertical and horizontal channels of an x-y recorder. These signals at the x-y recorder presented the modulation of the impedance of the eddy-current probe and was synchronized with the chopped laser beam. The signal also represented an image of the sample at the location of the probe. The present inventive technique uses the absolute resistance and inductance of detector coil 16 vs. the arbitrary proportional signals of the prior art.

From fundamental theories of electromagnetism, the impedance of detector coil 16 can be expressed as:

$$Z = 1/I^2 \int (E \times H) ds$$

where I is the current in detector coil 16, E and H are the electric and magnetic fields induced by coil 16, and s is the area enclosed by the electromagnetic field. Coil 16 impedance Z is normally expressed as a complex quantity, $Z = R + jX_L$. The resistance R, where R Re(Z) is the real component of the impedance Z and the reactance $X_L$ where $X_L = Im(Z)$ is the imaginary component. R and $X_L$ can be measured by a precision LCR impedance meter.

The impedance change due to laser induced thermal strain and elastic strain in specimen 14 can be expressed as:

$$\Delta Z = 1/I^2 \int (\partial \sigma/\partial T\, E^2 + j\omega \partial \mu/\partial T\, H^2) dT ds$$

where $\partial \sigma/\partial T$ is the electric conductivity ($\sigma$) change and $\partial \mu/\partial T$ is the magnetic permeability ($\mu$) change of the material due to induced thermoelastic effect T.

For example, the coil 16 impedance Z of a 100 kHz pancake probe at ambient temperature is experimentally measured to be: Resistance $R = 14.3\Omega$ and Reactance $X_L = 82.5\Omega$. The coil 16 impedance change $\Delta Z$, due to laser induced thermoelastic effects to the material is measured to be approximately $3\Omega$ or 20% for resistance and $4\Omega$ or 6% for reactance. Coordinating the impedance change with respect to specimen position, will allow advanced characterization of thermoelastic and defect properties of the material.

To those skilled in the art, many modifications and variations of the present invention are possible in light of the above teachings. It is therefore to be understood that the present invention can be practiced otherwise than as specifically described herein and still will be within the spirit and scope of the appended claims.

I claim:

1. An apparatus for advanced characterization of a material specimen comprising:
   a laser;
   a modulator modulating said laser;
   a scanning mirror for directing a beam from said laser on said material specimen thereby inducing thermal and elastic strains in said specimen;
   an eddy current detecting coil adjacent said specimen for detecting changes in electrical conductivity in said specimen caused by said thermal and elastic strains in said specimen;
   an impedance gain/phase analyzer, for measuring said the absolute resistance and inductance of said coil as a result of said changes in electrical conductivity in said specimen, connected to said detecting coil;
   a lock-in amplifier connected to said modulator; and
   a system controller for data acquisition and control connected to said impedance gain/phase analyzer, said lock-in amplifier and said scanning mirror.

2. The apparatus of claim 1 wherein said scanning mirror directs said beam on said specimen in a raster fashion.

3. A method for advanced characterization of a material specimen comprising the steps of:
   positioning said specimen adjacent an eddy current detecting coil;
   generating a modulated thermal source;
   directing said modulated thermal source onto said specimen at a localized area on said specimen;
   scanning said localized area across said specimen to cause generation of thermal and stress wave in said specimen;
   detecting with said coil changes in electrical conductivity and magnetic permeability in the localized areas caused by localized thermal and stress changes in said specimen; and
   measuring the absolute resistance and inductance of said coil so as to thereby directly characterize said material specimen.

4. The method of claim 3 wherein said scanning is done in a raster fashion across said specimen.

* * * * *